United States Patent
Li et al.

(10) Patent No.: US 10,913,052 B1
(45) Date of Patent: Feb. 9, 2021

(54) SUPPORTED BIMETALLIC CORE-SHELL STRUCTURE CATALYST AND ITS PREPARATION METHOD

(71) Applicant: BEIJING UNIVERSITY OF CHEMICAL TECHNOLOGY, Beijing (CN)

(72) Inventors: Dianqing Li, Beijing (CN); Rui Ma, Beijing (CN); Yufei He, Beijing (CN); Yongjun Feng, Beijing (CN); Junting Feng, Beijing (CN)

(73) Assignee: BEIJING UNIVERSITY OF CHEMICAL TECHNOLOGY, Beijing (CN)

( * ) Notice: Subject to any disclaimer, the term of this patent is extended or adjusted under 35 U.S.C. 154(b) by 7 days.

(21) Appl. No.: 16/493,275

(22) PCT Filed: Nov. 2, 2018

(86) PCT No.: PCT/CN2018/113555
§ 371 (c)(1),
(2) Date: Sep. 11, 2019

(87) PCT Pub. No.: WO2020/082410
PCT Pub. Date: Apr. 30, 2020

(30) Foreign Application Priority Data

Oct. 23, 2018 (CN) .......................... 2018 1 1234759

(51) Int. Cl.
*B01J 23/52* (2006.01)
*B01J 23/46* (2006.01)
(Continued)

(52) U.S. Cl.
CPC ............... *B01J 23/52* (2013.01); *B01J 21/04* (2013.01); *B01J 21/08* (2013.01); *B01J 23/468* (2013.01);
(Continued)

(58) Field of Classification Search
None
See application file for complete search history.

(56) References Cited

FOREIGN PATENT DOCUMENTS

| CN | 101516550 A | 8/2009 |
| CN | 103172097 A | 6/2013 |

(Continued)

OTHER PUBLICATIONS

Mazumder, Vismadeb et al., "Core/Shell Pd/FePt Nanoparticles as an Active and Durable Catalyst for the Oxygen Reduction Reaction" Journal of American Chemical Society; vol. 132, No. 23; (2010); pp. 7848-7849.

(Continued)

*Primary Examiner* — Colin W. Slifka
(74) *Attorney, Agent, or Firm* — J.C. Patents (57) ABSTRACT

The purpose of the invention is to provide a supported bimetallic core-shell structure catalyst and its preparation method. Supporter, metal salt and reducing agent solution are mixed to synthesize the catalyst M@PdM/ZT by using a one-step synthesis method, wherein the active metal particle M@PdM as core-shell structure, M Is the core representing one of the Ag, Pt, Au and Ir. ZT is the supporter, representing one of hydrotalcite ($Mg_2Al$-LDH), alumina ($Al_2O_3$) and silica ($SiO_2$). By changing the temperature and the reaction time to control the kinetic behavior of the reduction of two kinds of metal ions to realize the construction of core-shell structure. Active metal particle composition and shell thickness are regulated by controlling metal ion concentration. The bimetallic core-shell catalyst prepared by this method showed excellent selectivity and stability in acetylene selective hydrogenation and anthraquinone hydrogenation.

2 Claims, 9 Drawing Sheets

(51) Int. Cl.
*B01J 27/236* (2006.01)
*B01J 21/08* (2006.01)
*B01J 21/04* (2006.01)
*B01J 37/34* (2006.01)
*B01J 37/16* (2006.01)
*B01J 37/02* (2006.01)
*B01J 37/00* (2006.01)
*B01J 37/06* (2006.01)
*C07C 5/09* (2006.01)
*B01J 23/50* (2006.01)

(52) U.S. Cl.
CPC ............. *B01J 23/50* (2013.01); *B01J 27/236* (2013.01); *B01J 37/009* (2013.01); *B01J 37/0221* (2013.01); *B01J 37/0236* (2013.01); *B01J 37/06* (2013.01); *B01J 37/16* (2013.01); *B01J 37/343* (2013.01); *C07C 5/09* (2013.01); *C07C 2521/04* (2013.01); *C07C 2521/08* (2013.01); *C07C 2521/10* (2013.01); *C07C 2523/50* (2013.01); *C07C 2523/52* (2013.01)

(56) References Cited

FOREIGN PATENT DOCUMENTS

| | | |
|---|---|---|
| CN | 104226331 A | 12/2014 |
| CN | 103977794 B | 1/2016 |
| CN | 107052359 A | 8/2017 |
| CN | 108579758 A | 9/2018 |
| WO | 2018/122569 A1 | 7/2018 |

OTHER PUBLICATIONS

Meng, Min et al., "Integration of Kinetic Control and Lattice Mismatch to Synthesize Pd@AuCu Core-Shell Planar Tetrapods with Size-Dependent Optical Properties" Journal of Nano Letters; vol. 16; (2016); pp. 3036-3041.

The International Search Report of corresponding international application No. PCT/CN2018/113555, dated Apr. 29, 2019.

SUPPORTED BIMETALLIC CORE-SHELL STRUCTURE CATALYST AND ITS PREPARATION METHOD

CROSS-REFERENCE TO RELATED APPLICATION

This application is a national phase application of international application No. PCT/CN2018/113555 filed on Nov. 2, 2018, which in turn claims the priority benefits of Chinese application No. 201811234759.0, filed on Oct. 23, 2018. The contents of these prior applications are hereby incorporated by reference in their entirety.

TECHNICAL FIELD

The present disclosure relates to the field of catalyst preparation, in particular to a supported bimetallic core-shell structure catalyst and its preparation method.

BACKGROUND ART

As the basis of energy conversion, heterogeneous catalysis plays an important role in the national economy, new and efficient supported catalysts have been an important force to promote the development of multiphase catalysis. Due to the synergistic effect between the two metals (including geometric effect and electronic effect), bimetallic catalysts have adjustable composition and structure. It is widely used in selective hydrogenation, oxidation, hydrolysis and reforming reactions.

Bimetallic catalysts can be divided into alloy structure, heterogeneous structure and core-shell structure according to the distribution of the two metals. Due to the difference of core-shell composition, the composition of bimetallic core-shell structure is more diverse, and highly adjustable. Compared with alloy structure, core-shell structure has its unique chemical properties such as electron transfer between nuclear and shell layers, lattice strain of surface metal atoms, and full exposure of active metal on the surface. However, core-shell structure with single metal shell M@N (M and N represent one metal each) has poor stability, and it is difficult to maintain structural stability under harsh reaction conditions. Therefore, design and synthesis a bimetallic core-shell structure with bimetallic alloy shell and single metal core is necessary, this kind of structure have the advantages of core-shell structure as well as the stability of alloy which is important for improving the performance of bimetallic catalytic materials.

However, the controllable preparation of this kind of materials is still a challenge. In recent years, it has been reported that the supported core-shell structure is prepared by crystal seed epitaxial. Min Meng, etc, Nano Letters, 2016, 16, 3036, prepared a Pd@AuCu core-shell structure through the regulation of ion reduction kinetics of Au and Cu ions, wherein, Pd cube as crystal seed, hexadecyl trimethylammonium chloride as ending agent, and glucose as reducing agent. Vismadeb Mazumder etc, JACS, 2010, 132, 7848, obtained Pd@PtFe nanoparticles by growing FePt alloy on the surface of Pd nanoparticles with the presence of surfactant by two-step method. However, epitaxial growth method has the disadvantages such as: complicated preparation methods and the active sites is often covered by surfactant residues. Therefore, designing a simple and feasible one-step method to prepare M@NM bimetallic core shell structure without surfactant and protectant is still one of the difficulties in the field of nanomaterials.

In conclusion, supported core-shell structure has a high research value in the field of multiphase catalysis due to its unique structural characteristics, and radiates to the fields of electrocatalysis, photocatalysis and optical devices. However, the preparation methods reported in existing literatures have some shortcomings, such as complicated reaction conditions, difficult operation, high cost and so on. Therefore, the controllable preparation of supported core-shell bimetallic catalysts and the application of such catalysts in heterogeneous catalytic reactions still need to be further studied.

SUMMARY

The purpose of the invention is to provide a supported bimetallic core-shell structure catalyst and its preparation method. It has been used in petroleum and fine chemical industry and has good application effect for selective hydrogenation of acetylene and anthraquinone. Supported bimetallic core-shell catalyst provided by the invention is expressed as M@PdM/ZT, active metal particles M@PdM are core-shell structures, M Is the core with a diameter of 5-15 nm, representing one of the Ag, Pt, Au and Ir; PdM alloy is the shell structure with a thickness of 1-10 nm; ZT is the supporter, representing one of hydrotalcite ($Mg_2Al$-LDH), alumina ($Al_2O_3$) and silica ($SiO_2$);

The preparation method of supported bimetallic core-shell catalyst provided by the invention has the following steps:

A. M salt and Pd salt are added to the reducing solution to obtain mixed salt solution after ultrasonic irradiation for 4-5 min; wherein the total concentration of M and Pd ions is 0.01-20 mmol/L, the molar ratio of the M:Pd ions is 0.1 to 10;

The M is one of Ag, Pt, Au and Ir; M salt is one of $AgNO_3$, $HPtCl_6$, $Pt(C_5H_7O_2)_2$, $H_2IrCl_6 \cdot 6H_2O$, $Ir(C_5H_7O_2)_3$ and $HAuCl_4 \cdot 4H_2O$; Pd salt is one of the $PdCl_2$, $Pd(NO_3)_2$, $Pd(C_5H_7O_2)_2$, $Pd(CH_3COO)_2$; the reducing solution is a mixture of reducing agent and deionized water, wherein, the mass ratio of deionized water is 0-20%; the reducing agent is one of ethylene glycol, isopropanol, N, n-dimethyl acetamide, N, n-dimethyl formamide and glyceraldehyde.

Figure 1:
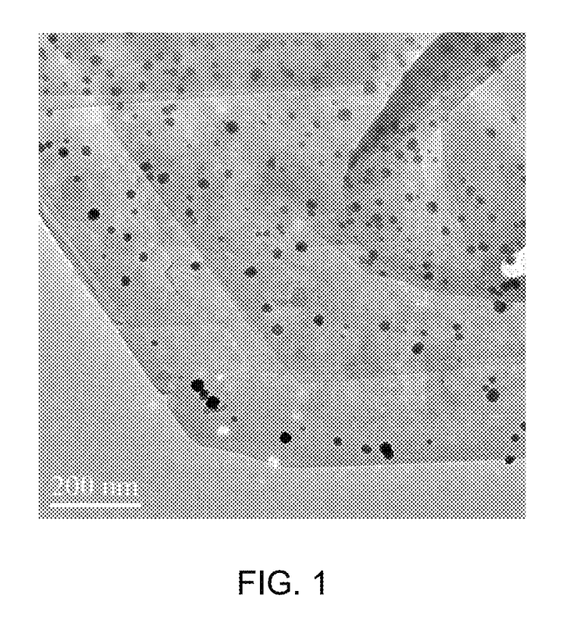
FIG. 1 is the electron microscope image of catalyst Ag@PdAg/Mg$_2$Al-LDH prepared by embodiment 1.

B. Mixed salt solution obtained in A is stirred and heated for 10-30 min under 40-50° C., add the supporter and continue to stir for 10-20 min, heat up the temperature to 100-160° C. and keep it for 0.5-24 h to obtain black precipitate suspension, drop to room temperature to obtain gray or black powder after centrifuging, washing and drying; It is proved as catalyst M@PdM/ZT by characterization; its metal active ingredient particles are core-shell structure, wherein M is the core and PdM alloy is the shell. The supporter is one of alumina ($Al_2O_3$), silica ($SiO_2$) and hydrotalcite ($Mg_2Al$-LDH);

FIG. 1 is the electron microscope image of catalyst Ag@PdAg/$Mg_2Al$-LDH prepared by embodiment 1. It can be seen that the metal active ingredient particles in the supported catalyst are evenly dispersed on hydrotalcite supporter, and crystal shape and size of metal particles are intact, with an average particle size of 15.6 nm.

Figure 2:
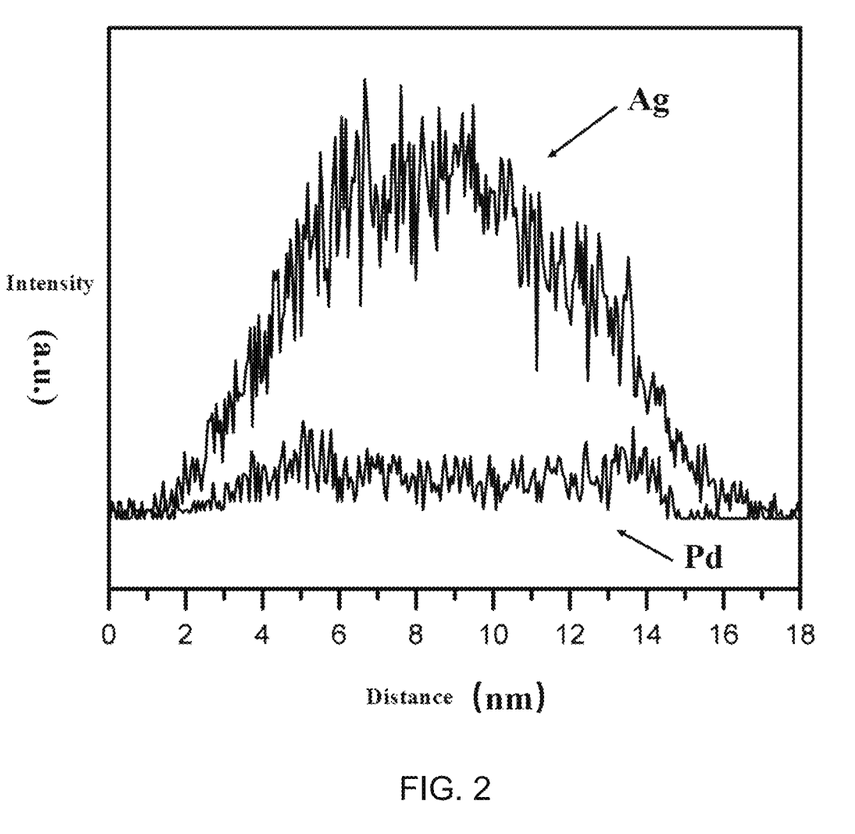
FIG. 2 is the EDX linear sweep results of metal Pd and Ag in metal particles of catalyst Ag@PdAg/Mg$_2$Al-LDH prepared by embodiment 1.

FIG. 2 shows the EDX linear sweep results of metal Pd and Ag in metal particles of catalyst Ag@PdAg/$Mg_2Al$-LDH prepared by embodiment 1. By comparing the distribution of Pd and Ag, it can be seen that Ag is distributed throughout the metal particles while Pd is concentrated on the surface of the metal particles. Therefore, it can be concluded that the metal active ingredient particles of this catalyst is core-shell structures that PdAg coated on the surface of Ag. In addition, it can be seen from the linear sweep results of element Pd in FIG. 2 that the shell thickness of PdAg alloy is 4 nm and the core diameter is 8 nm.

Figure 3:
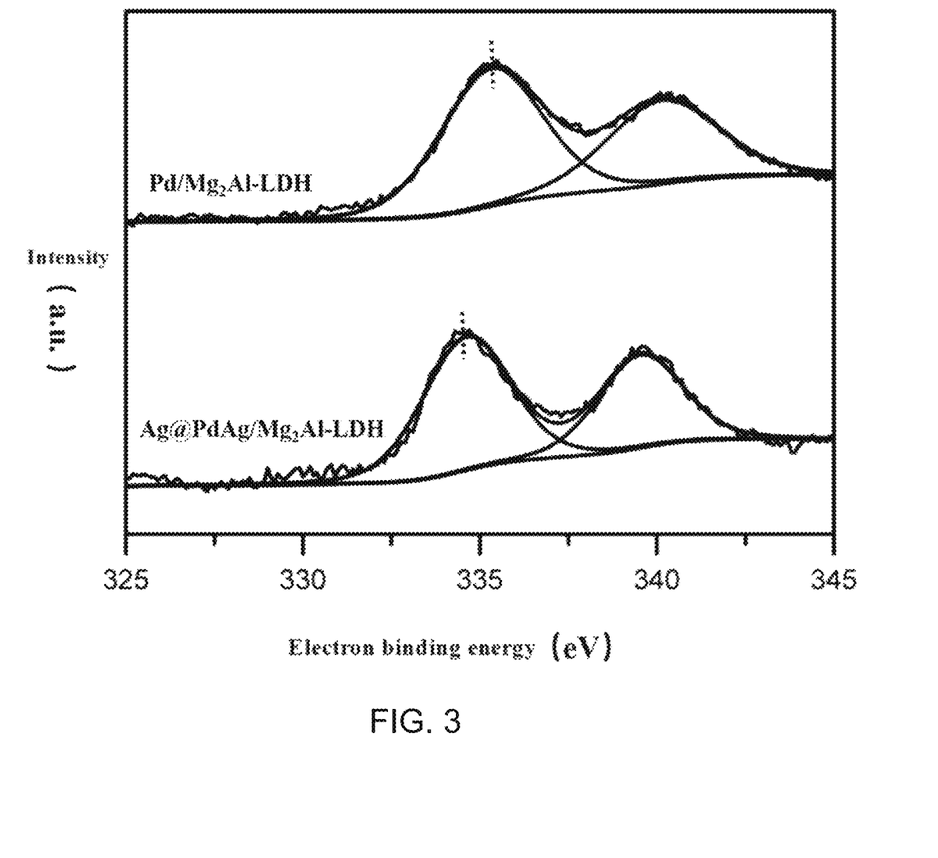
FIG. 3 is the X-ray photoelectron spectroscopy of Pd in catalyst Ag@PdAg/Mg$_2$Al-LDH prepared by embodiment 1.

FIG. 3 shows the X-ray photoelectron spectroscopy of Pd in catalyst Ag@PdAg/Mg$_2$Al-LDH prepared by embodiment 1. Compared with single metal, Pd electron binding energy shift indicates that PdAg alloy is formed on the surface of prepared catalyst metal particles.

Figure 4:
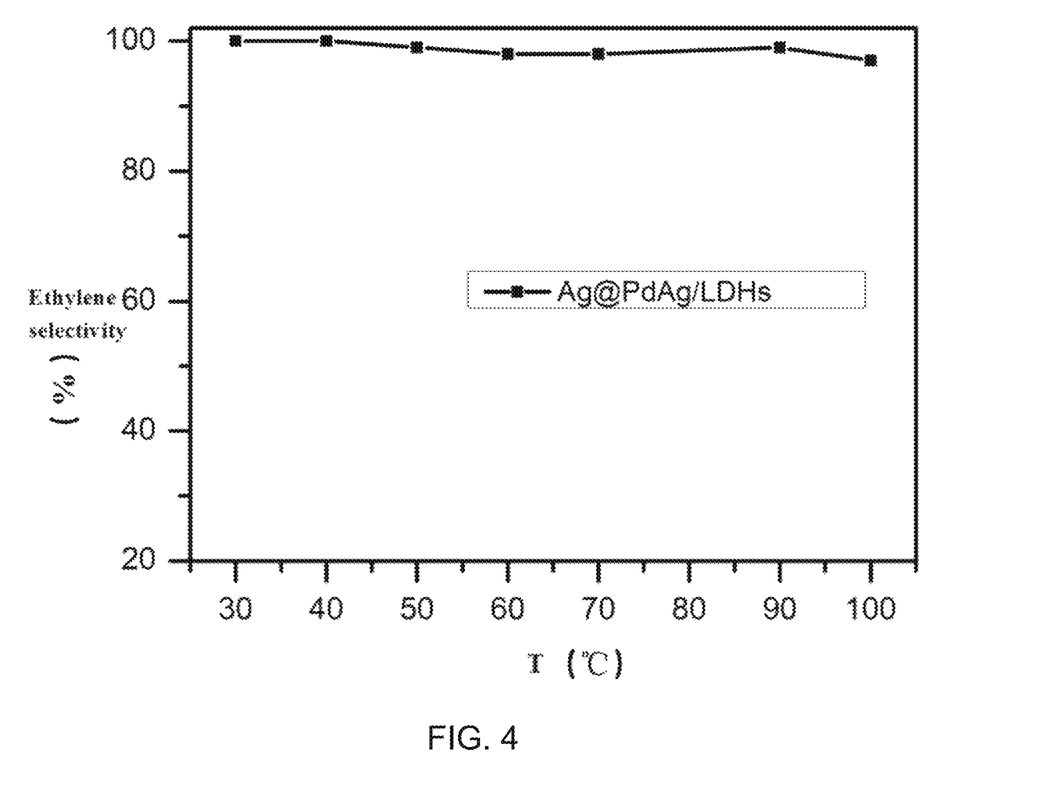
FIG. 4 is the changing curve of ethylene selectivity with temperature in selective hydrogenation of acetylene when using the catalyst Ag@PdAg/Mg$_2$Al-LDH prepared by embodiment 1.

FIG. 4 shows the changing curve of ethylene selectivity with temperature in selective hydrogenation of acetylene when using the catalyst Ag@PdAg/Mg$_2$Al-LDH prepared by embodiment 1. The selectivity of ethylene is higher than 95% in the range of 30-100° C. temperature.

Figure 5:
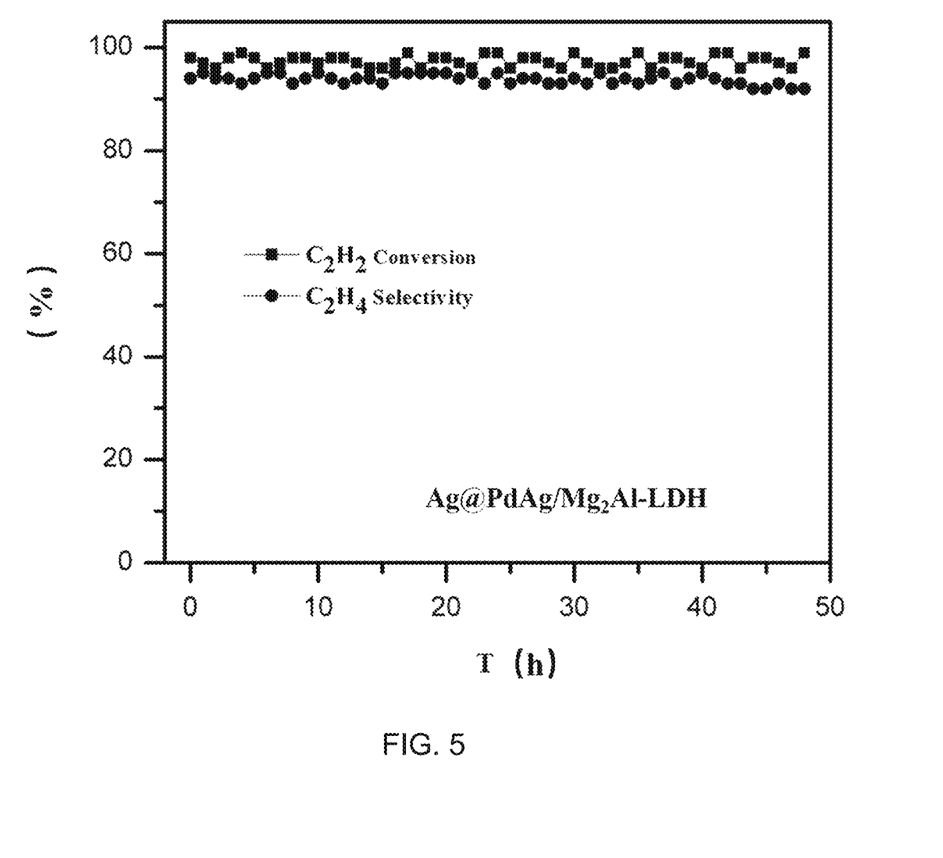
FIG. 5 is the changing curve of acetylene conversion and ethylene selectivity with time in selective hydrogenation of acetylene when using the catalyst Ag@PdAg/Mg$_2$Al-LDH prepared by embodiment 1.

FIG. 5 shows the changing curve of acetylene conversion and ethylene selectivity with time in selective hydrogenation of acetylene when using the catalyst Ag@PdAg/Mg$_2$Al-LDH prepared by embodiment 1. As can be seen from the figure, the catalyst did not deactivate after the reaction for 50 h, and the acetylene conversion rate remained above 96%. The selectivity of ethylene shows a similar trend and remained above 93% after long reaction time.

Figure 6:
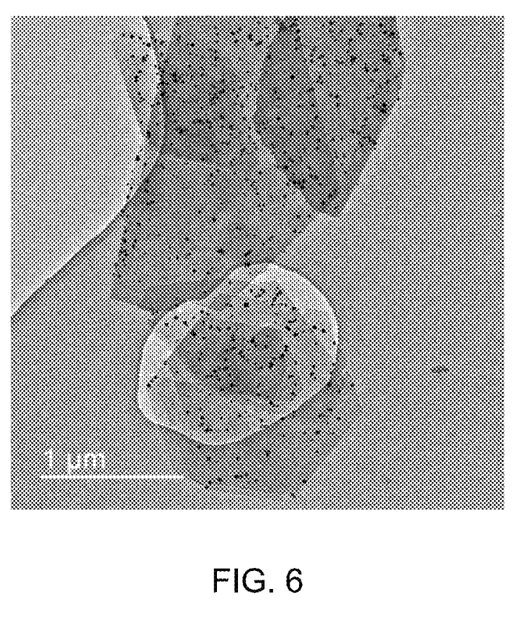
FIG. 6 is the electron microscope image of catalyst Ag@PdAg/Mg$_2$Al-LDH prepared by embodiment 1 after 48 h selective hydrogenation of acetylene.

FIG. 6 is the electron microscope image of catalyst Ag@PdAg/Mg$_2$Al-LDH prepared by embodiment 1 after 48 h selective hydrogenation of acetylene. It can be seen from the figure that after a long time of reaction, there is no agglomeration of metal particles in the catalyst, and the metal active ingredient particles are evenly dispersed on the surface of hydrotalcite supporter.

Figure 7:
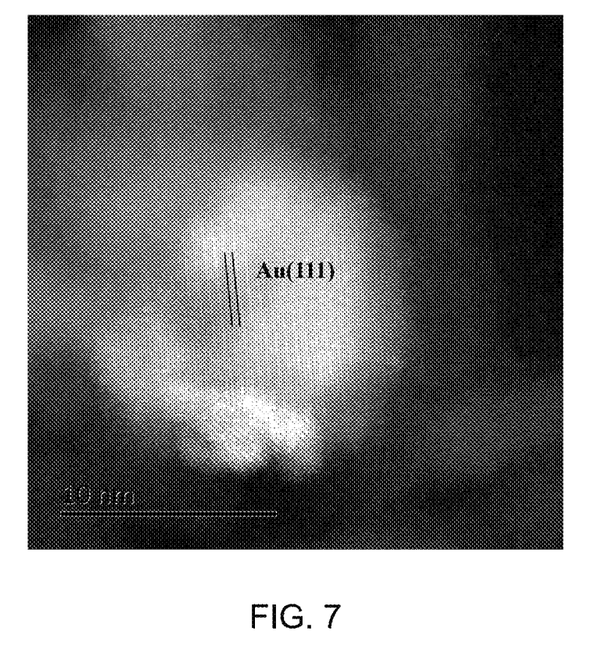
FIG. 7 is the scanning transmission electron microscope (STEM) photo of metal particles of catalyst Au@PdAu/SiO$_2$ prepared by embodiment 2.

FIG. 7 is a scanning transmission electron microscope (STEM) photo of metal particles of catalyst Au@PdAu/SiO$_2$ prepared by embodiment 2. As can be seen from the photo, metal particle size of Au@PdAu is about 15 nm. The brightness of metal particles bulk phase and surface is different (the brightness of STEM photos is determined by the atomic number of metal atoms, the larger the atomic number, the brighter it is), the surface brightness of metal particles is lower than the central part, indicating that metal Pd is concentrated on the surface of metal particles. In addition, by measuring the lattice fringe, it can be known that the bulk phase of the metal particle is Au, that is, the metal particle is a core-shell structure with Au as the core and PdAu as the shell, the shell thickness is about 2 nm.

Figure 8:
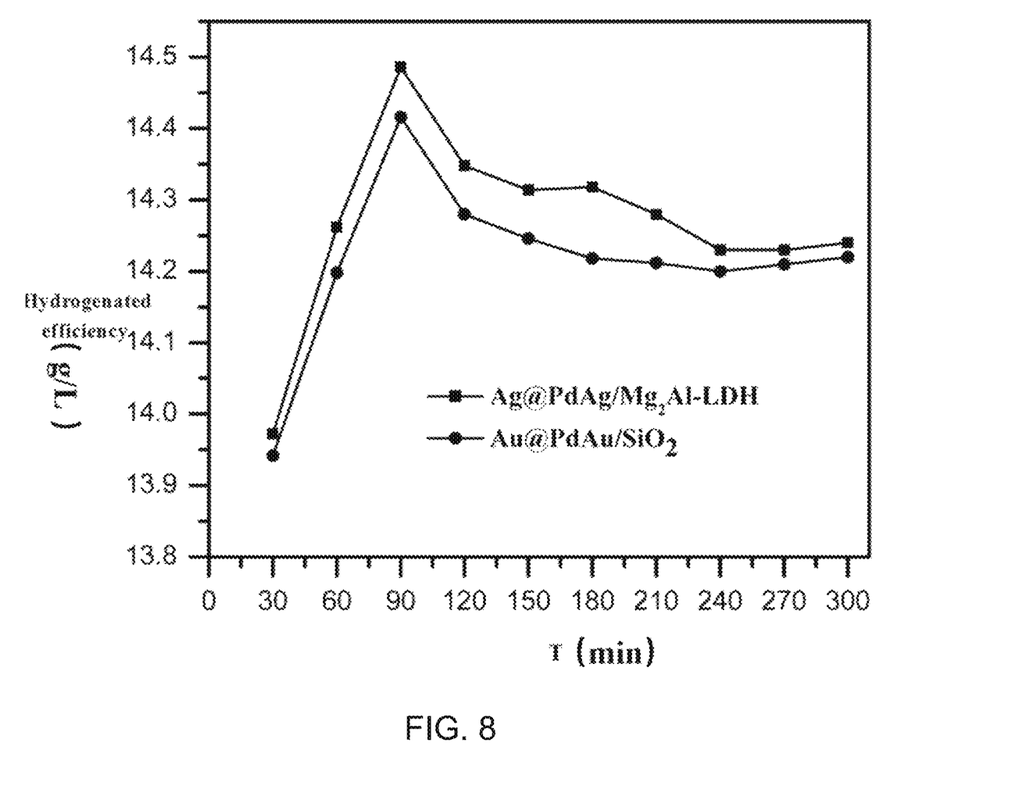
FIG. 8 is the changing curves of hydrogenation efficiency of the catalyst prepared by embodiment 1 and embodiment 2 in the hydrogenation of anthraquinone.

FIG. 8 shows the changing curves of hydrogenation efficiency of the catalyst prepared by embodiment 1 and embodiment 2 in the hydrogenation of anthraquinone. The initial hydrogenation efficiency of both catalysts can reach 13.9 g/L. Moreover, the hydrogenation efficiency of the catalyst remained above 14.2 g/L after the reaction for 300 min, indicating that the bimetallic core-shell catalyst had excellent stability in reaction.

Figure 9:
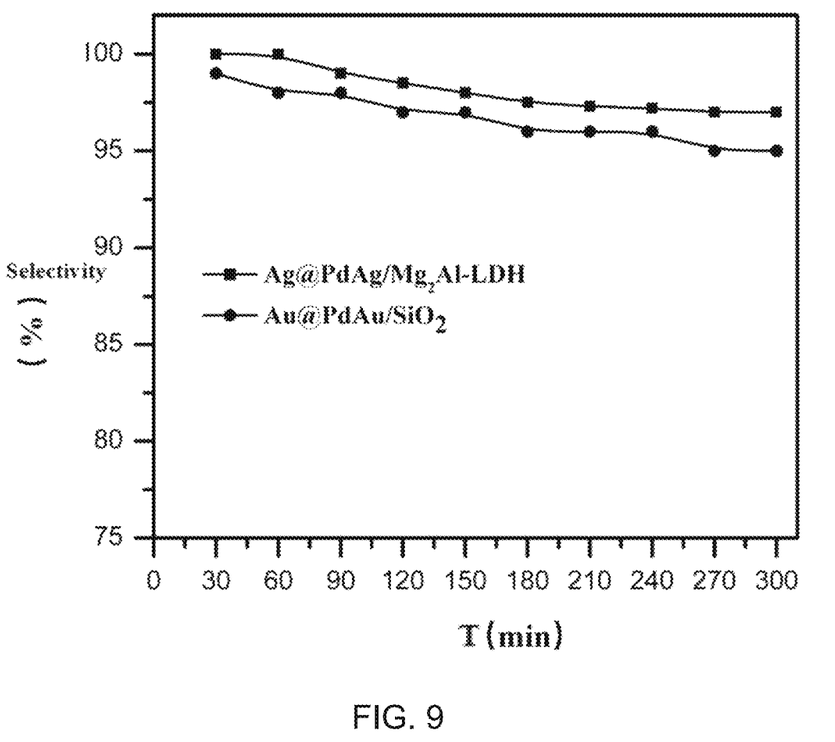
FIG. 9 is the changing curves of effective anthraquinone selectivity with time of the catalyst prepared by embodiment 1 and the embodiment 2 in the hydrogenation of anthraquinone.

FIG. 9 shows the changing curves of effective anthraquinone selectivity with time of the catalyst prepared by embodiment 1 and the catalyst prepared by embodiment 2 in the hydrogenation of anthraquinone. As can be seen from the figure, the effective anthraquinone selectivity of the core-shell structure catalyst remained above 95% after 5 h reaction.

The beneficial effect of the invention is: the supporter, metal salt and reducing agent solution are mixed to synthesize the catalyst M@PdM/ZT by using a one-step synthesis method, wherein active metal particle M@PdM as core-shell structure, and the shell is PdM alloy. By changing the temperature and the reaction time to control the kinetic behavior of the reduction of two kinds of metal ions to realize the construction of core-shell structure; Active metal particle composition and shell thickness are regulated by controlling metal ion concentration. This method is simple and universal, which can not only fully expose the reactive sites of active metals, but also give full play to the synergistic effect between the two metals. The bimetallic core-shell catalyst prepared by this method showed excellent selectivity and stability in acetylene selective hydrogenation and anthraquinone hydrogenation.

PREFERRED EMBODIMENTS

The present invention is further described in detail in combination with the appended drawings.

Embodiment 1

Add 0.008 mmol Pd(C$_5$H$_7$O$_2$)$_2$, 0.08 mmol AgNO$_3$ into 100 ml N,N-Dimethylformamide to obtain mixed salt solution after 5 min ultrasonic irradiation. Pure the mixed solution in a flask and put it on an oil bath for stirring and heating for 10 min under 50° C., add 1 g Mg$_2$Al-LDH and continue to stir for 10 min, heat up the temperature to 130° C. and keep it for 2 h to obtain black precipitate suspension, drop to room temperature to obtain black powder after centrifuging, washing and drying. It is proved as catalyst Ag@PdAg/Mg$_2$Al-LDH by characterization; its metal active ingredient particles are core-shell structure, wherein PdAg alloy is the shell.

Embodiment 2

Add 0.01 mmol Pd(CH$_3$COO)$_2$, 0.04 mmoln HAuCl$_4$.4H$_2$O into 100 ml Eethylene glycol aqueous solution (the mass ratio of deionized water is 20%) to obtain mixed salt solution after 5 min ultrasonic irradiation with stirring. Pure the mixed solution in a flask and put it on an oil bath for stirring and heating for 0.5 h under 50° C., add 0.5 g amorphous silica powder and continue to stir for 10 min, heat up the temperature to 110° C. and keep it for 12 h to obtain black precipitate suspension, drop to room temperature to obtain black powder after centrifuging, washing and drying. It is proved as catalyst Au@PdAu/SiO$_2$ by characterization; its metal active ingredient particles are core-shell structure, wherein PdAu alloy is the shell.

Embodiment 3

Add 0.002 mmol Pd(NO$_3$)$_2$, 0.06 mmolAgNO$_3$ into 100 ml N,N-dimethylformamide aqueous solution (the mass ratio of deionized water is 10%) to obtain mixed salt solution after 5 min ultrasonic irradiation with stirring. Pure the mixed solution in a flask and put it on an oil bath for stirring and heating for 1 h under 40° C., add 1 g Al$_2$O$_3$ powder and continue to stir for 10 min, heat up the temperature to 130° C. and keep it for 2 h to obtain black precipitate suspension, drop to room temperature to obtain gray powder after centrifuging, washing and drying. It is proved as catalyst Ag@PdAg/Al$_2$O$_3$ by characterization; its metal active ingredient particles are core-shell structure, wherein PdAg alloy is the shell.

Embodiment 4

Add 0.005 mmol Ir(C$_5$H$_7$O$_2$)$_3$, 0.001 mmolPdCl$_2$ into 100 ml isopropanol aqueous solution (the mass ratio of deionized water is 10%) to obtain mixed salt solution after 5 min ultrasonic irradiation with stirring. Pure the mixed solution in a flask and put it on an oil bath for stirring and heating for 0.5 h under 40° C., add 2 g Mg$_2$Al-LDH powder and continue to stir for 10 min, heat up the temperature to 100° C. and keep it for 1 h to obtain black precipitate suspension, drop to room temperature to obtain gray powder after centrifuging, washing and drying. It is proved as catalyst Ir@PdIr/Mg$_2$Al-LDH by characterization; its metal active ingredient particles are core-shell structure, wherein PdIr alloy is the shell.

Embodiment 5

Add 0.01 mmol Pd(CH$_3$COO)$_2$, 0.004 mmolHPtCl$_6$ into 100 ml N,N-dimethylacetamide solution to obtain mixed salt solution after 5 min ultrasonic irradiation with stirring. Pure the mixed solution in a flask and put it on an oil bath for stirring and heating for 0.5 h under 45° C., add 2 g Al$_2$O$_3$ powder and continue to stir for 10 min, heat up the temperature to 160° C. and keep it for 12 h to obtain black precipitate suspension, drop to room temperature to obtain black powder after centrifuging, washing and drying. It is proved as Pt@PdPt/Al$_2$O$_3$ catalyst by characterization; its metal active ingredient particles are core-shell structure, wherein PdPt alloy is the shell.

Application Example 1

Evaluate the performance of acetylene selective hydrogenation of the catalyst in embodiment 1-5 and the comparison sample.

The evaluation device is WFS-3015 microreactor of Tianjin xianquan instrument co. LTD. The operation steps are as follows:

0.1 g catalyst samples are weighed, mixed with 1.9 g quartz sand (40-80 mesh) and placed in quartz reaction tubes. Before the reaction, raise the temperature of reaction bed to 150° C. and process the catalyst pretreatment with nitrogen for 1 hour. The nitrogen flow rate is 50 ml/min. After the pretreatment and the reaction bed temperature drops to room temperature, feed nitrogen, ethylene acetylene mixture and hydrogen with the flow rate of 111, 55.5 and 1.0 ml/min respectively. The percentage of acetylene in ethylene-acetylene mixture is 0.947%, and the ratio of hydrogen acetylene is about 2. Control the reaction temperature is 100° C., the reaction airspeed is 10050 h$^{-1}$, and the relative pressure of the reaction system is 0.4 MPa. The concentrations of reactants and products are analyzed by online gas chromatography, capillary column is 0.53*50 mm and the detector adopts hydrogen flame detector. Normalization method is adopted for data processing. The results of acetylene conversion and ethylene selectivity of catalyst under 100° C. are shown in table 1:

TABLE 1

| Catalyst sample | Embodiment 1 | Embodiment 2 | Embodiment 3 | Embodiment 4 | Embodiment 5 | comparison |
|---|---|---|---|---|---|---|
| Acetylene conversion (%) | 100 | 94 | 87 | 100 | 100 | 86 |
| Ethylene selectivity (%) | 94 | 91 | 100 | 74 | 91 | 72 |

Wherein, the comparison is catalyst PdPtAg/Mg$_2$Al-LDH which is disclosed in CN103977794B, this catalyst is specially designed for selective hydrogenation of acetylene.

Application Example 2

Evaluate the performance anthraquinone hydrogenation of the catalyst in embodiment 1-5 and the comparison sample.

The evaluation device is PTFE internal tank reactor with magnetic stirring and heating device, 25 g catalyst and 60 ml anthraquinone working solution (100 g/L anthraquinone working solution is composed of 100 g 2-ethyl anthraquinone, 1,3, 5-tritoluene and 400 mL trioctyl phosphate) are added to the reactor and sealed, injecting hydrogen into the reactor through a cylinder to replace the air, repeat 5 times. Heat up the reactor to 50° C., fill with hydrogen, make the pressure reach 0.3 MPa and adjust the stirring speed to 1200 rpm/min, then start to timing. After the 1.5 h reaction, the reaction samples are collected from the reaction gas outlet valve for activity and selectivity evaluation and the yield of H$_2$O$_2$ is calculated. The yield of H$_2$O$_2$ and spatio-temporal yield of catalyst are shown in table 2.

TABLE 2

| Catalyst sample | Embodiment 1 | Embodiment 2 | Embodiment 3 | Embodiment 4 | Embodiment 5 | comparison |
| --- | --- | --- | --- | --- | --- | --- |
| yield of $H_2O_2$ (g/mL) | 14.30 | 13.58 | 13.09 | 14.10 | 12.69 | 11.00 |
| Spatio-temporal yield ($gH_2O_2/(gPd \cdot h)$) | 2884 | 2715 | 2618 | 2618 | 2538 | 2200 |

Wherein, the comparison is catalyst $Pd/Al_2O_3$ which is disclosed in CN103172097A, this catalyst is specially designed for anthraquinone hydrogenation.

What is claimed is:

1. A preparation method of supported bimetallic core-shell catalyst comprising:
adding M salt and Pd salt to a reducing solution to obtain a mixed salt solution after ultrasonic irradiation for 4-5 min; wherein a total concentration of M and Pd ions is 0.01-20 mmol/L, a molar ratio of M:Pd ions is 0.1 to 10; M is one of Ag, Pt, Au and Ir; M salt is one of $AgNO_3$, $HPtCl_6$, $Pt(C_5H_7O_2)_2$, $H_2IrCl_6 \cdot 6H_2O$, $Ir(C_5H_7O_2)_3$ and $HAuCl_4 \cdot 4H_2O$; Pd salt is one of the $PdCl_2$, $Pd(NO_3)_2$, $Pd(C_5H_7O_2)_2$, $Pd(CH_3COO)_2$; the reducing solution is a mixture of reducing agent and deionized water, wherein, a mass ratio of the deionized water is 0-20%; the reducing agent is one of ethylene glycol, isopropanol, N, n-dimethyl acetamide, N, n-dimethyl formamide and glyceraldehyde; stirring and heating the mixed salt solution for 10-30 min under 40-50° C., adding a supporter and continuing to stir for 10-20 min; raising temperature to 100-160° C. and keeping the temperature for 0.5-24 h to obtain a black precipitate suspension; dropping to room temperature to obtain gray or black powders after centrifuging, washing and drying; wherein the gray or black powders are catalyst M@PdM/ZT containing metal active ingredient particles dispersed on the supporter; the metal active ingredient particles are of a core-shell structure with M being the core and PdM alloy being the shell; the supporter is one of alumina ($Al_2O_3$), silica ($SiO_2$) and hydrotalcite ($Mg_2Al$-LDH).

2. A supported bimetallic core-shell catalyst M@PdM/ZT comprising metal active ingredient particles dispersed on a supporter, wherein the active metal ingredient particles contain M and PdM alloy and are of a core-shell structure; M is the core with a diameter of 5-15 nm, and selected from the group consisting of Ag, Pt, Au and Ir; PdM alloy is the shell with a thickness of 1-10 nm; ZT is the supporter, and selected from the group consisting of hydrotalcite ($Mg_2Al$-LDH), alumina ($Al_2O_3$) and silica ($SiO_2$).

* * * * *